(12) United States Patent
Dürr

(10) Patent No.: US 9,962,241 B2
(45) Date of Patent: May 8, 2018

(54) ENDOSSEOUS SINGLE TOOTH IMPLANT

(71) Applicant: Epiphanostics GmbH, Holzkirchen (DE)

(72) Inventor: Walter Dürr, Remchingen (DE)

(73) Assignee: Epiphanostics GmbH, Holzkirchen (DE)

( * ) Notice: Subject to any disclaimer, the term of this patent is extended or adjusted under 35 U.S.C. 154(b) by 52 days.

(21) Appl. No.: 14/363,970

(22) PCT Filed: Dec. 9, 2012

(86) PCT No.: PCT/DE2012/100375
§ 371 (c)(1),
(2) Date: Jun. 9, 2014

(87) PCT Pub. No.: WO2013/083125
PCT Pub. Date: Jun. 13, 2013

(65) Prior Publication Data
US 2014/0356813 A1    Dec. 4, 2014

(30) Foreign Application Priority Data

Dec. 9, 2011   (DE) ................. 10 2011 056 253
Sep. 7, 2013   (DE) .................. 20 2012 103 424 U

(51) Int. Cl.
*A61C 8/00*   (2006.01)

(52) U.S. Cl.
CPC .......... *A61C 8/0062* (2013.01); *A61C 8/0066* (2013.01); *A61C 8/0068* (2013.01); *A61C 8/0069* (2013.01)

(58) Field of Classification Search
CPC ......... A61C 8/00; A61C 8/005; A61C 8/0066; A61C 8/0069; A61C 8/0062–8/69
USPC ........................... 433/172–176; 606/300–321
See application file for complete search history.

(56) References Cited

U.S. PATENT DOCUMENTS

| 4,960,381 A | 10/1990 | Niznick |
| 5,015,186 A | 5/1991 | Detsch |
| 5,026,285 A | 6/1991 | Dürr et al. |
| 5,106,299 A * | 4/1992 | Ghalili ................. A61C 8/0048 433/172 |

(Continued)

FOREIGN PATENT DOCUMENTS

| DE | 41 27 839 A1 | 3/1992 |
| DE | 40 28 855 C2 | 12/1992 |

(Continued)

OTHER PUBLICATIONS

Espacenet, English translated Abstract of DE 40 28 855 A1, printed on Jun. 9, 2014.

(Continued)

*Primary Examiner* — Yogesh Patel
(74) *Attorney, Agent, or Firm* — Cahn & Samuels, LLP

(57) ABSTRACT

The invention concerns a single tooth implant for a fixed tooth replacement having a substantially cylindrical base body which can be inserted into a bore made in a jaw bone, an abutment which can be inserted into the annular recess of the base body and having a bore for receiving a holding screw and a fixing head for the tooth replacement, and a holding screw which can be inserted into the blind bore in the base body and which passes through the abutment.

23 Claims, 12 Drawing Sheets

(56) References Cited

U.S. PATENT DOCUMENTS

Figure 1:
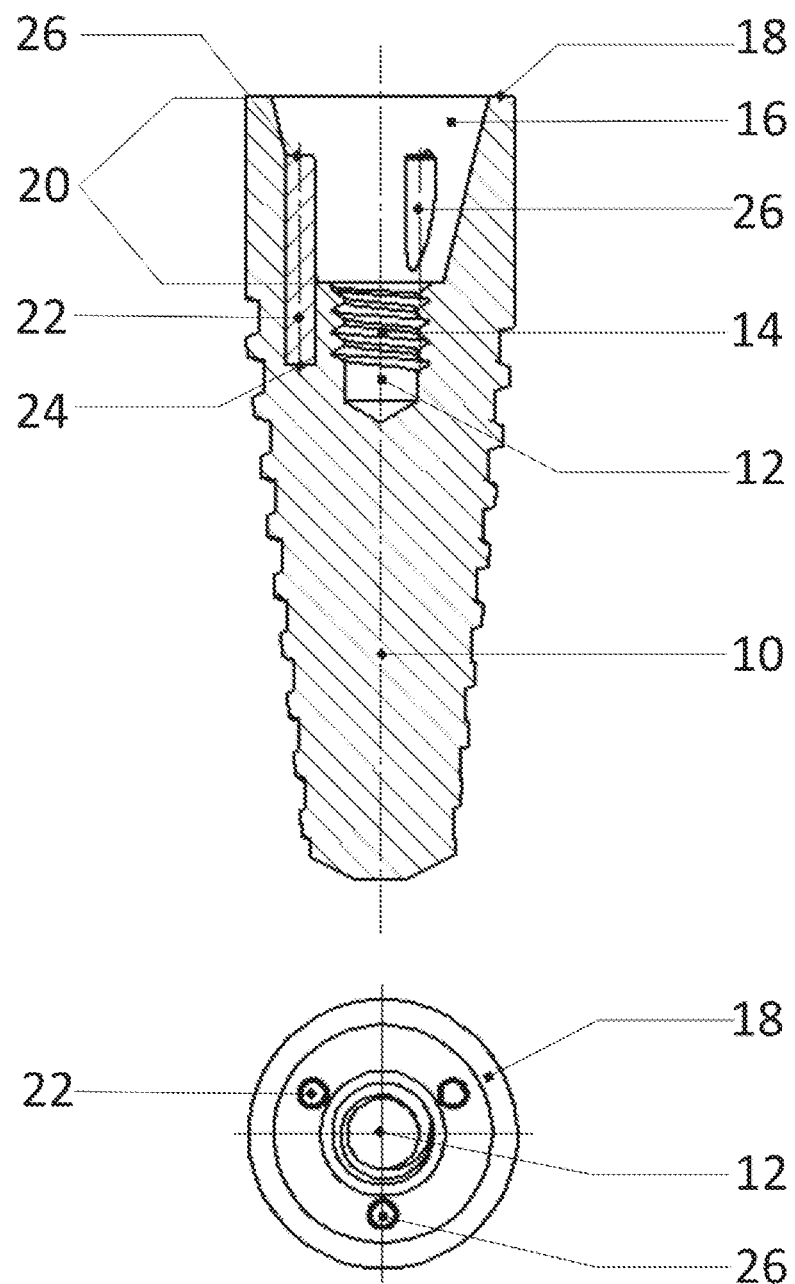

| | | | | |
|---|---|---|---|---|
| 5,302,126 | A * | 4/1994 | Wimmer | A61C 8/0022 433/173 |
| 5,674,072 | A * | 10/1997 | Moser | A61C 8/0022 433/173 |
| 5,823,776 | A | 10/1998 | Duerr et al. | |
| 5,908,298 | A | 6/1999 | Dürr et al. | |
| 5,989,026 | A * | 11/1999 | Rogers | A61C 8/005 433/172 |
| 7,682,152 | B2 * | 3/2010 | Ford | A61C 8/0086 433/169 |
| 2003/0113690 | A1 | 6/2003 | Hollander | |
| 2004/0101807 | A1 * | 5/2004 | Porter | A61C 8/0001 433/173 |
| 2006/0246398 | A1 * | 11/2006 | Groll | A61C 8/0006 433/173 |
| 2007/0059666 | A1 * | 3/2007 | Zickman | A61C 8/005 433/173 |
| 2008/0182227 | A1 * | 7/2008 | Wolf | A61C 8/005 433/174 |
| 2010/0248181 | A1 * | 9/2010 | Kremer | A61B 17/888 433/152 |
| 2010/0285427 | A1 * | 11/2010 | Hung | A61C 8/0089 433/174 |
| 2014/0356813 | A1 * | 12/2014 | Durr | A61C 8/0066 433/173 |

FOREIGN PATENT DOCUMENTS

| | | |
|---|---|---|
| DE | 195 09 762 A1 | 9/1996 |
| DE | 195 34 979 C1 | 1/1997 |
| DE | 37 35 378 C2 | 9/1998 |

OTHER PUBLICATIONS

Espacenet, English translated Abstract of DE 195 09 762, printed on Jun. 9, 2014.
Espacenet, English translated Abstract of DE 37 35 378 A1, printed on Jun. 9, 2014.
Espacenet, English translated Abstract of 41 27 839 A1, printed on Jun. 9, 2014.
Espaenet, English translated Abstract of 195 34 979 C1, printed on Jun. 9, 2014.
International Preliminary Report on Patentability (English translation) for PCT/DE2012/100375, dated Jun. 27, 2014.

* cited by examiner

Fig. 3
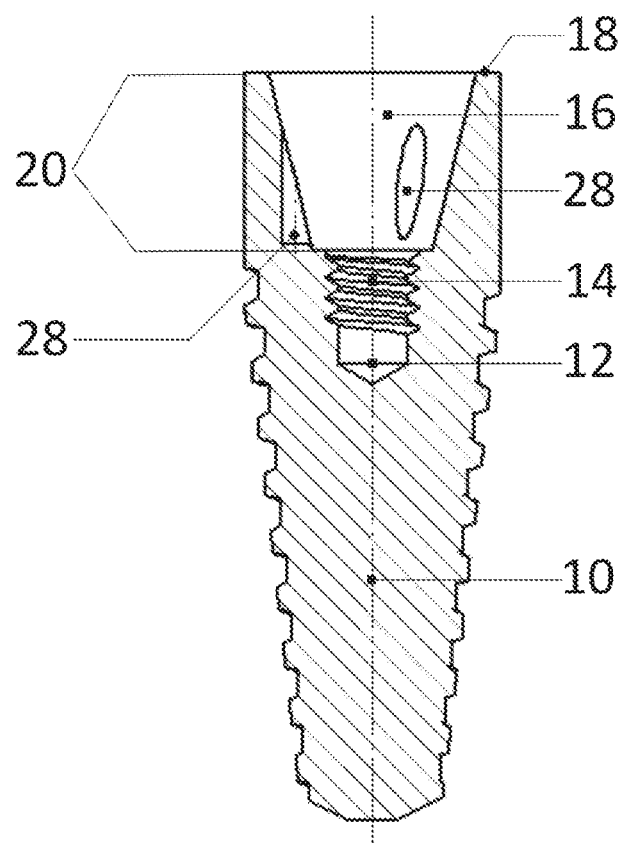
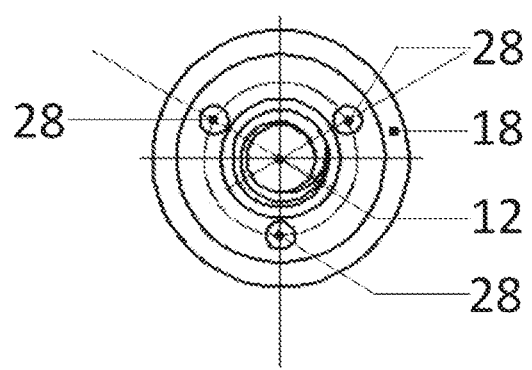

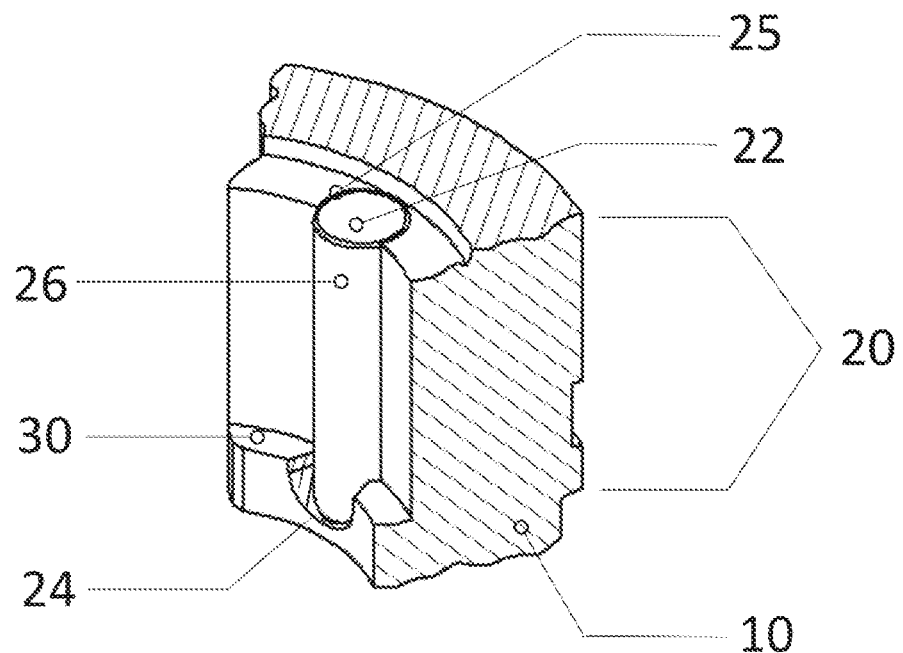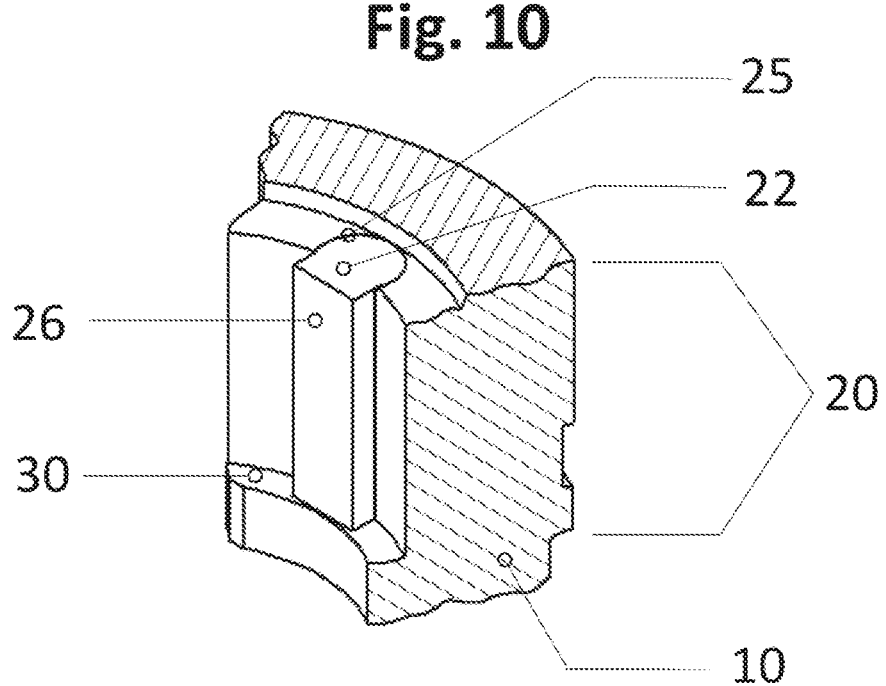

ENDOSSEOUS SINGLE TOOTH IMPLANT

This application is the National Stage of International Application No. PCT/DE2012/100375, filed on Dec. 9, 2012, which claimed the benefit of German Application No. 10 2011 056 253.2 filed Dec. 9, 2011 and German Application No. 20 2012 103 424.7 filed Sep. 7, 2012, which are hereby incorporated by reference. The International Application No. PCT/DE2012/100375 was published on Jun. 13, 2013.

I. FIELD OF INVENTION

The invention concerns a single tooth implant for a fixed tooth replacement.

II. BACKGROUND OF THE INVENTION

In a single tooth implant as is known from DE 40 28 855 C2 and is also the subject-matter of DE 195 09 762.9-32 rotation prevention is effected in such a way that the base body positively locking elements at the bottom of the annular recess of the base body and the spacer sleeve positively locking elements which are complementary thereto are provided at the cervical edge of the centering shoulder of the spacer sleeve. From the point of view of production engineering such positively locking elements can only be produced with comparative difficulty, while in many situations of use it is not especially desirable that it is not the full depth of the annular recess or the centering shoulder that is available for centering, fixing and securing the spacer sleeve relative to the base body.

Another dental implant as is provided in DE 37 35 378 also involves difficulties of a similar kind, which are due to the fact that in that case also the positively locking elements of the base body are disposed at a spacing from the coronal edge thereof within a blind bore in the base body.

DE 41 27 839 A1 discloses an implant base body whose central annular recess has a positively locking element which directly adjoins the coronal edge of the base body, wherein the positively locking element is of a groove-shaped configuration and the holding portion to be inserted in the base body is of a configuration complementary thereto. A separate implant post is not provided in that case.

DE 195 34 979 C1 discloses a single tooth implant in which the positively locking elements of the base body are arranged directly adjoining the coronal edge thereof with a corresponding arrangement and configuration of the abutment positively locking elements which are complementary thereto. Because the entire depth of the annular recess of the base body is available for centering and guiding the abutment that is said to give markedly improved stability in the connection between the spacer sleeve and the base body with a greater degree of design freedom in the nature of the division and the shaping of the positively locking elements.

III. SUMMARY OF THE INVENTION

The invention now develops the implants known in the state of the art such as to ensure improved guidance and centering of the abutment in the base body with manufacture being simplified at the same time.

According to the invention in a development of the endosseous single tooth implant of the general kind set forth that object is attained by at least one embodiment according to the invention. Particular configurations of the invention are subject-matter of the detailed description.

More precisely the invention concerns an endosseous single tooth implant for a fixed tooth replacement, comprising a substantially cylindrical base body which can be inserted into a bore made in a jaw bone and having an annular recess with a positively locking portion and a bore which is open towards its coronal end and which is arranged apically relative to the recess and which has a threaded portion which is arranged at the apical end in the base body for fixing a holding screw, an abutment which can be inserted into the recess of the base body and having a positively locking portion, with a bore for receiving the holding screw and a fixing head for the tooth replacement, and a holding screw which can be inserted into the blind bore in the base body and which passes through the abutment, wherein the positively locking portion of the base body has at least one base body positively locking element operative in the peripheral direction and the positively locking portion of the abutment has at least one abutment positively locking element complementary to the base body positively locking element, wherein the positively locking portion of the base body and the positively locking portion of the abutment are complementary to each other in such a shape that the abutment can be so inserted into the recess in the base body that the respective positively locking elements are brought into engagement with each other, wherein the mutually complementary positively locking elements are in the form of a male part—female part connection.

According to the invention the positively locking portion of the base body and the positively locking portion of the abutment are matched to each other in such a shape that the abutment can be so inserted into the recess in the base body that the respective positively locking elements can be brought into engagement with each other and thus prevent a movement in the peripheral direction. The respective positively locking portions can be in the form of a truncated cone-like or hollow-cylindrical annular recess or bore, also with portions of differing diameters, in the base body, and an externally cylindrical portion or portions respectively corresponding thereto on the abutment. The following description of the elements of the invention applies in that respect for all respective embodiments unless stated to the contrary.

In a configuration according to the invention the positively locking portion of the base body can be in particular in the form of a hollow truncated cone, for example with a cone angle (non-locking) of 6° to 18°, in particular 10° to 16°, quite particularly 12° to 15°, in particular 14°, in each case relative to the longitudinal axis of the hollow truncated cone—the half-value of the angle of the cone tip—. In this case the positively locking portion of the abutment is in the form of a truncated cone corresponding to the hollow truncated cone.

In this embodiment the positively locking portion of the base body is in the form of a hollow truncated cone with a circular surface of a smaller diameter (top surface) and a circular surface of a larger diameter (base surface), wherein the longitudinal axis of the hollow truncated cone is arranged coaxially with the longitudinal axis of the base body, the circular surfaces delimit the hollow truncated cone and the circular surface of the larger diameter is towards the coronal end of the base body.

The positively locking portion of the base body can extend from the coronal end of the base body to the threaded portion for receiving the holding screw at the apical end of the base body. In particular the positively locking portion is of a length of up to two thirds of the total length of the hollow truncated cone of the base body, beginning at the threaded portion for receiving the holding screw. In this configuration the base body has an annular coronal end portion arranged around the central axis of the base body. In this embodiment it is possible to achieve particularly good centering and guidance of the frustoconical positively locking portion of the abutment when inserting the abutment into the base body, this providing for preventing rotation of the abutment. Thus, with this embodiment according to the invention, the functions of centring, guidance and rotational securing are combined in one functional element.

According to the invention the positively locking portion of the base body can have at least one, in particular at least two, quite particularly at least three, base body positively locking elements operative in the peripheral direction and the positively locking portion of the abutment respectively has an abutment positively locking element complementary to the base body positively locking element or elements. The positively locking elements are generally limited in their axial length by the length of the positively locking portion and, as mentioned above, generally leave free a sealing portion which is free of positively locking element at the coronal end of the positively locking portion in order to bring the conical surfaces into sealing contact in terms of their periphery when the holding screw is tightened. The frustoconical positively locking portion of the abutment can be of a greater axial length than the corresponding hollow cone portion in the base body so that it projects out of the base body. A seal can be provided in the sealing portion between the truncated cone on the abutment and the annular coronal end portion of the base body, for example an O-ring in a peripheral groove in the truncated cone on the abutment, which promotes the sealing action of the conical surfaces when the holding screw is tightened.

By virtue of the configuration according to the invention of the base body with the positively locking elements the base body can be screwed into the jaw bone by means of a tool engaging the positively locking elements, with a torque that is increased over the structures from the state of the art, and the abutment is reliably secured to prevent rotation after being inserted into the base body.

According to the invention the mutually complementary positively locking elements on the base body and the abutment are respectively in the form of a male part-female part connection, wherein the male part or parts is or are arranged on the base body. By virtue of the arrangement selected in that fashion, as a consequence of avoiding a reduction in the wall thickness of the base body, even in the case of ceramic materials it is possible to provide for precise force transmission which permits the use of fully or partially ceramic base body and/or abutment, besides the known metals and alloyed materials. It is however equally possible for the male part or parts to be arranged on the positively locking portion of the abutment and for the corresponding female parts to be arranged on the base body.

According to the invention the male part positively locking element can respectively be in the form of a tongue which extends parallel to the longitudinal axis of the base body and which engages in rotationally secured relationship in a respective corresponding female part on the other component. The positively locking elements can be machined out of the components consisting of the base body and the abutment by mechanical machining like milling, boring and so forth.

The positively locking portion can be of a cylindrical or conical configuration. In the case of a cylindrical structure the positively locking portion is formed on the abutment in the form of a cylindrical portion which is adapted with its outside diameter to the hollow-cylindrical bore on the base body in length and diameter.

In the configuration of the positively locking portions in the form of a hollow truncated cone on the base body and a truncated cone on the abutment the at least one tongue is of such a configuration that, according to the respective arrangement on the base body or the abutment, the tongue is raised radially about the longitudinal axis of the base body or the abutment and extends axially in wedge-shaped configuration relative thereto in the direction of the larger diameter of the truncated cone or the hollow truncated cone and in that case does not increase the diameter of the larger circular surface defining the truncated cone. The radial height of the tongue therefore corresponds at a maximum to the difference in the radii of the circular surfaces defining the truncated cone and the hollow truncated cone respectively.

According to the invention the tongue can advantageously be in the form of a pin respectively held in a blind bore (holding bore), wherein the blind bore is provided coaxially with the longitudinal central axis of the base body in the conical region of the hollow truncated cone or the truncated cone, depending on the respective relative position of the male and female parts in the base body or in the abutment, as far as the region parallel to the threaded portion. As a result of the conical surface on the hollow cone or truncated cone each pin is at least partially guided in a groove of a cross-section which decreases towards the end opposite to the holding bore, giving a kind of wedge shape for the tongue. To make the wall thickness in the positively locking portion as thick as possible, then, depending on the respective relative position of the male or female part in the base body or in the abutment, the blind bore for receiving the pin or groove is so arranged that the bore peripheral line tangentially touches the peripheral line of the circular surface at the apical end or the bore is partially arranged in the circular surface at the apical end.

The pins can each be of a preferably circular or regularly or irregularly polygonal cross-section, of which a cross-sectional segment projects from the groove in the conical wall radially in the direction of the longitudinal central axis, depending on the respective relative position of the male or female part, of the base body or the abutment, and can provide the tongue to over the maximum axial length of the positively locking portion. In the simplest form a pin can be of a cylindrical shape and can be produced for example in a wire drawing machine. Thus it is possible for the pin to be produced from a material with a higher level of tensile strength than the material for the abutment or the base body so that the force can be precisely transmitted by way of the positively locking elements or the screwing-in tool.

To axially secure the pin each pin can be fitted/inserted in the blind bore by way of a press fit.

To permit the abutment to be capable of being inserted in peripherally different positions the positively locking elements, with respect to the periphery of the abutment and the base body, can have a 30, 60, 90 or 120 degree graduation. In addition in that case the number of female part positively locking elements can be equal to or greater than that of the male part positively locking elements, for example depending on the respective sub division, being twice or three times the number.

As already mentioned, at the abutment side there can be provided a sealing means like an O-ring in a peripheral groove in the sealing portion or at the transition from the sealing portion and to the positively locking portion of the abutment in order to prevent ingress of foreign bodies and fluid into cavities in the implant after the implant has been fitted to the patient. If required a sealing means like an O-ring can additionally or alternatively be arranged in a groove at the base body side, the latter being less preferred.

If the sealing portion of the abutment and the end portion of the base body are in the form of mutually corresponding cones with the above-specified cone angle then, as described, a sealing means can also be arranged in a peripheral groove in the conical sealing surface.

A female thread can be provided for the implant post/holding screw in the blind bore apically from the conical positively locking and centering portion of the base body, wherein the holding screw can also pass completely through the abutment.

In addition the invention also concerns a base body and an abutment as individual components of the implant according to the invention, which are overall of a configuration corresponding to the design details for the implant.

It is an essential aspect of the present invention that the base body and the abutment with the respectively corresponding positively locking elements in the form of the above-described tongue-and-groove connection in a centering and guide region can be manufactured by simplified mechanical machining. Machining of the blanks is substantially simplified and less expensive in comparison with the solutions known in the state of the art.

Thus the invention is also directed to the use of a positively locking connection in the manner of a tongue-and-groove connection for rotationally secured connection of implant portions, wherein the tongue-and-groove connection is made by a pin held in a bore on an implant component engaging in positively locking relationship into a corresponding groove on a second implant component, the positively locking connection being made in a truncated cone-hollow truncated cone component pair. Wherever multi-part implants are used, which have to be prevented from rotating, it is possible to use the positively locking connection according to the invention.

IV. BRIEF DESCRIPTION OF THE DRAWINGS

Figure 2:
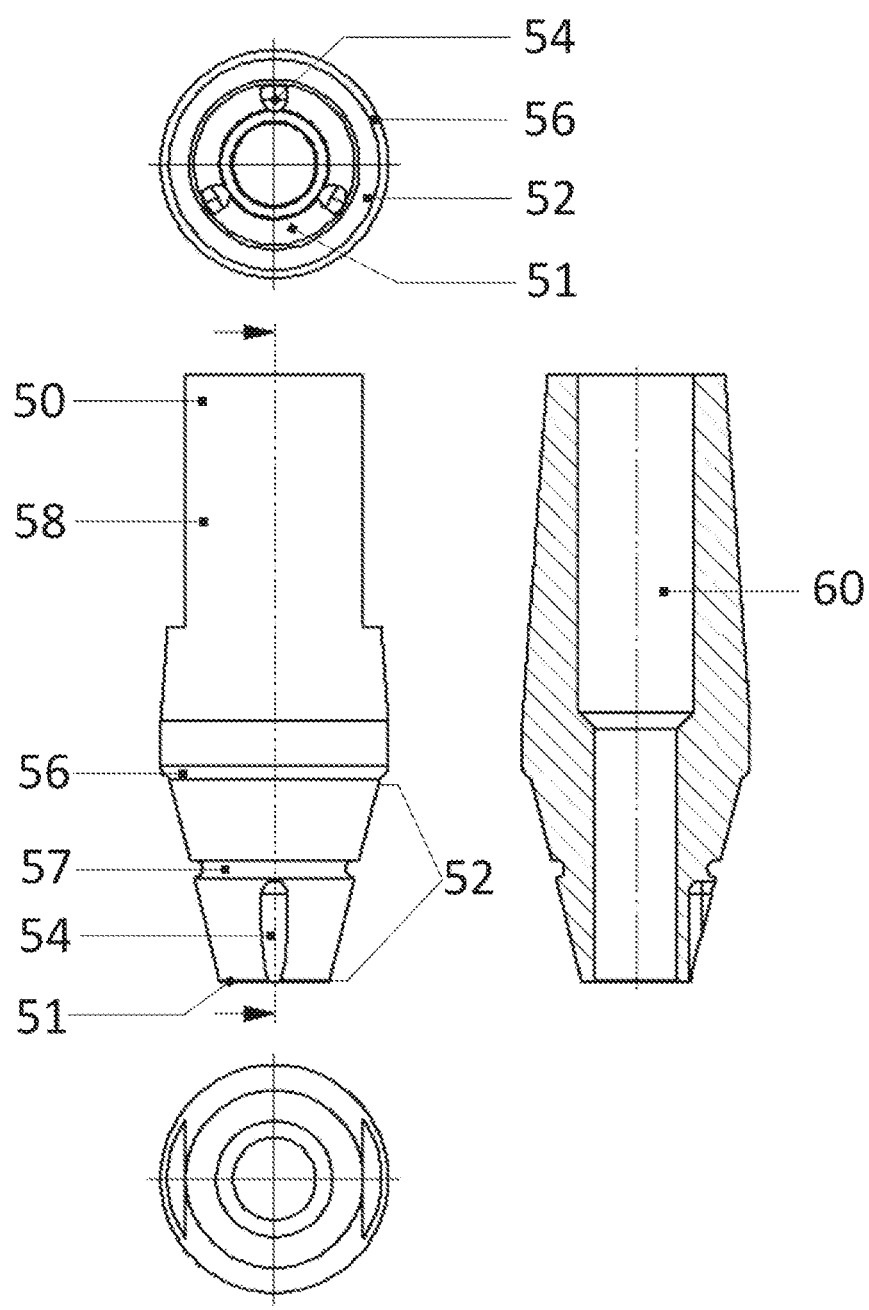
Figure 4:
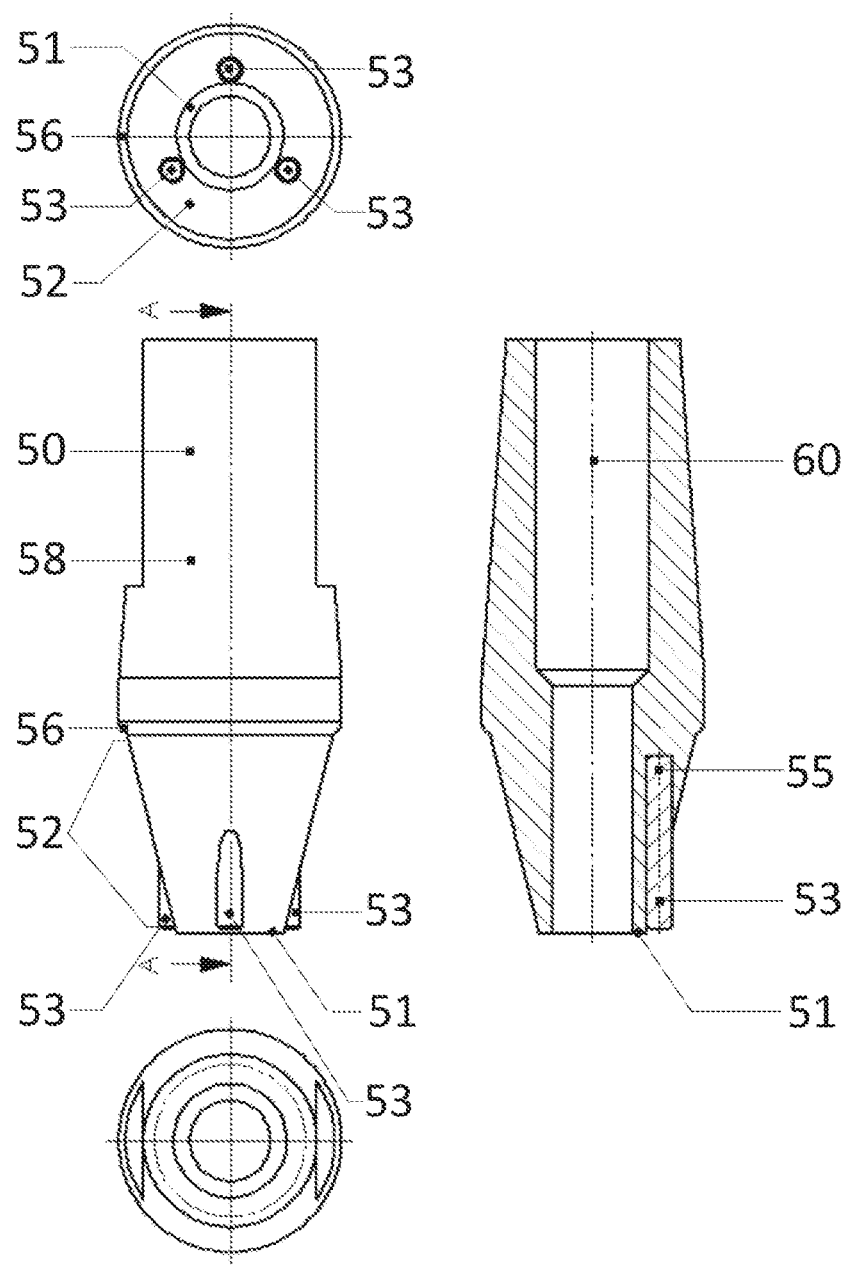
Figure 5:
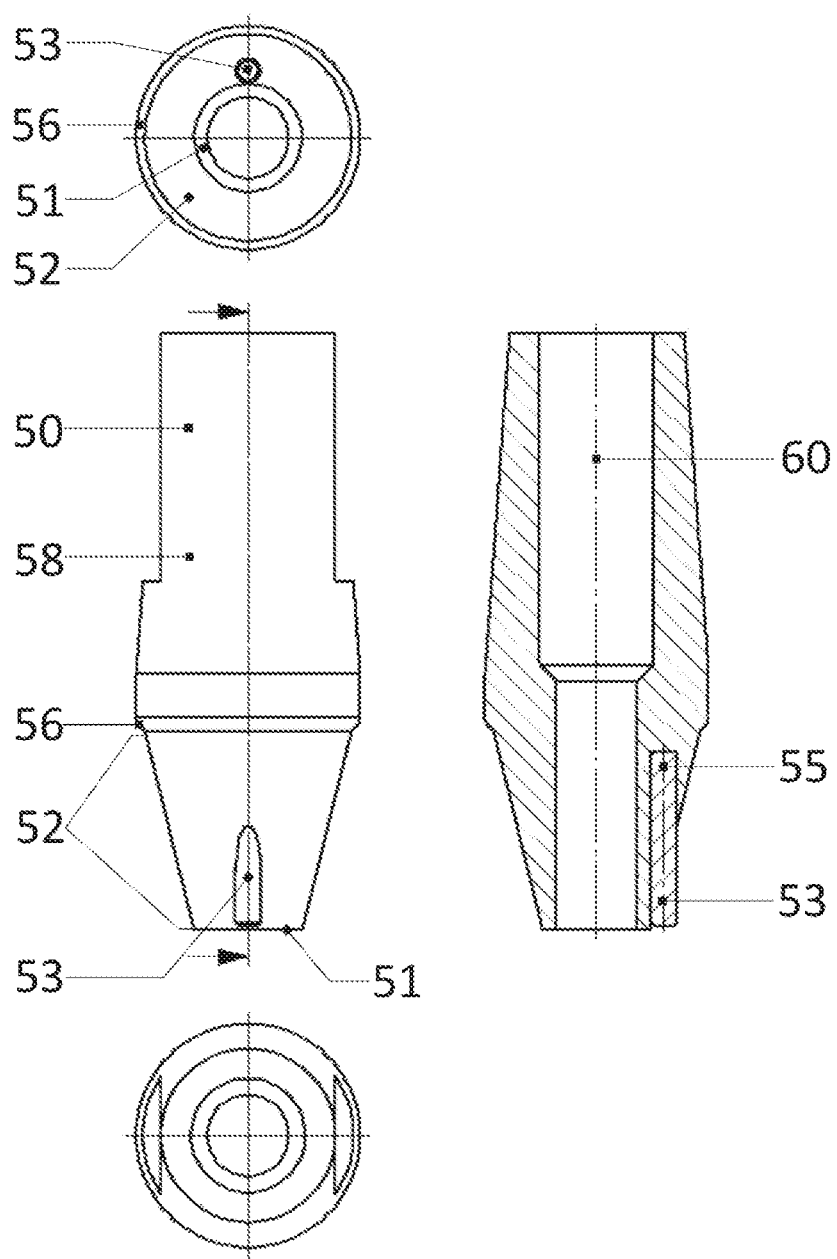
Figure 6:
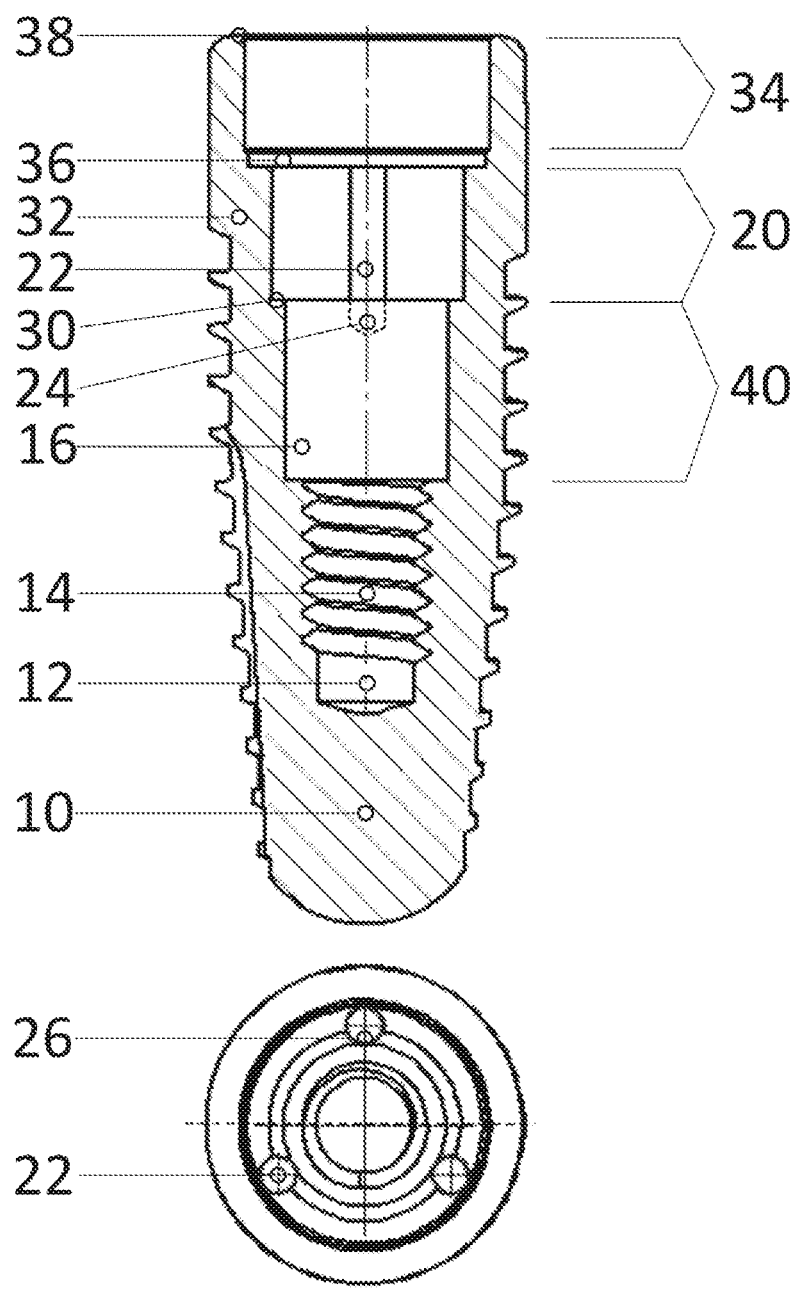
Figure 7:
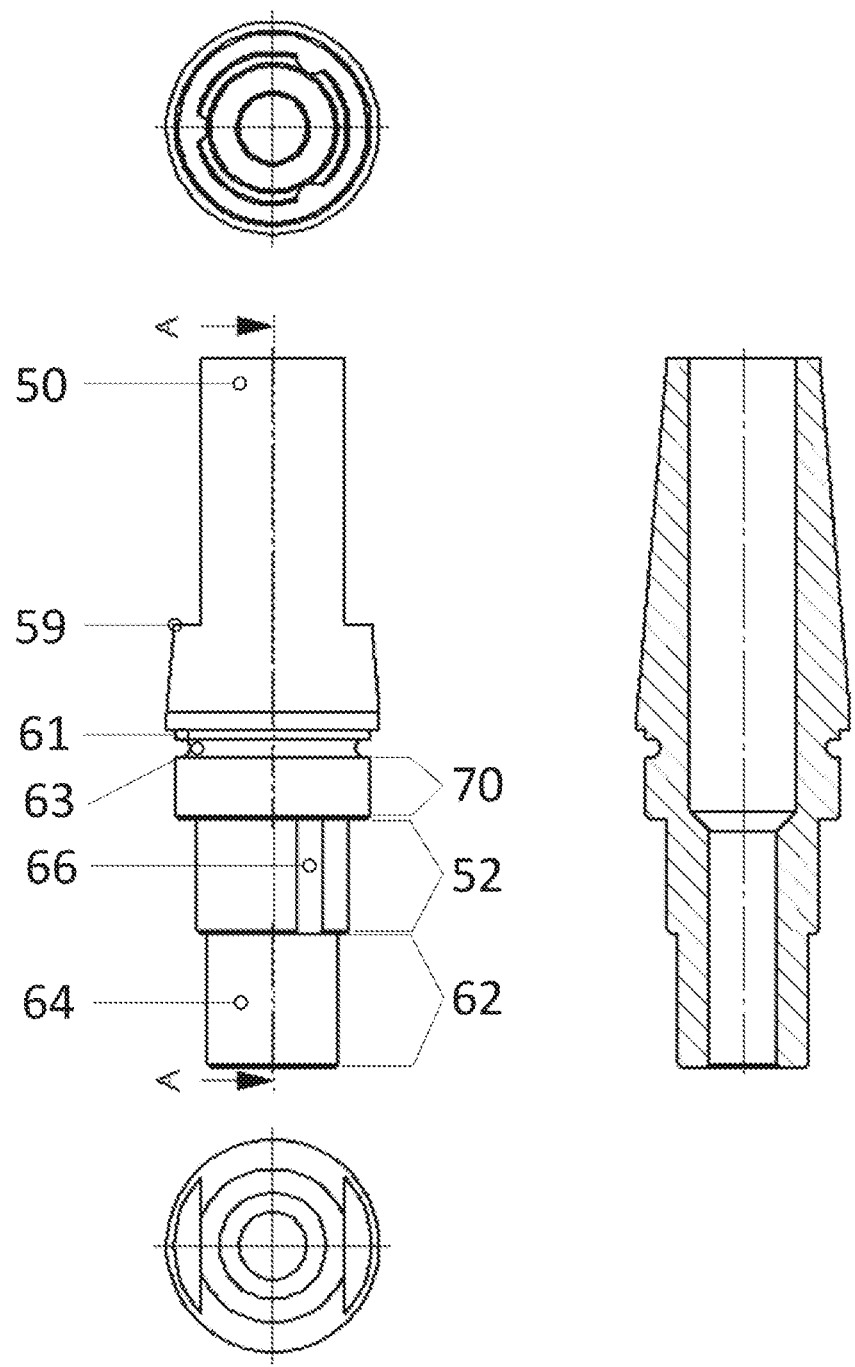
Figure 8:
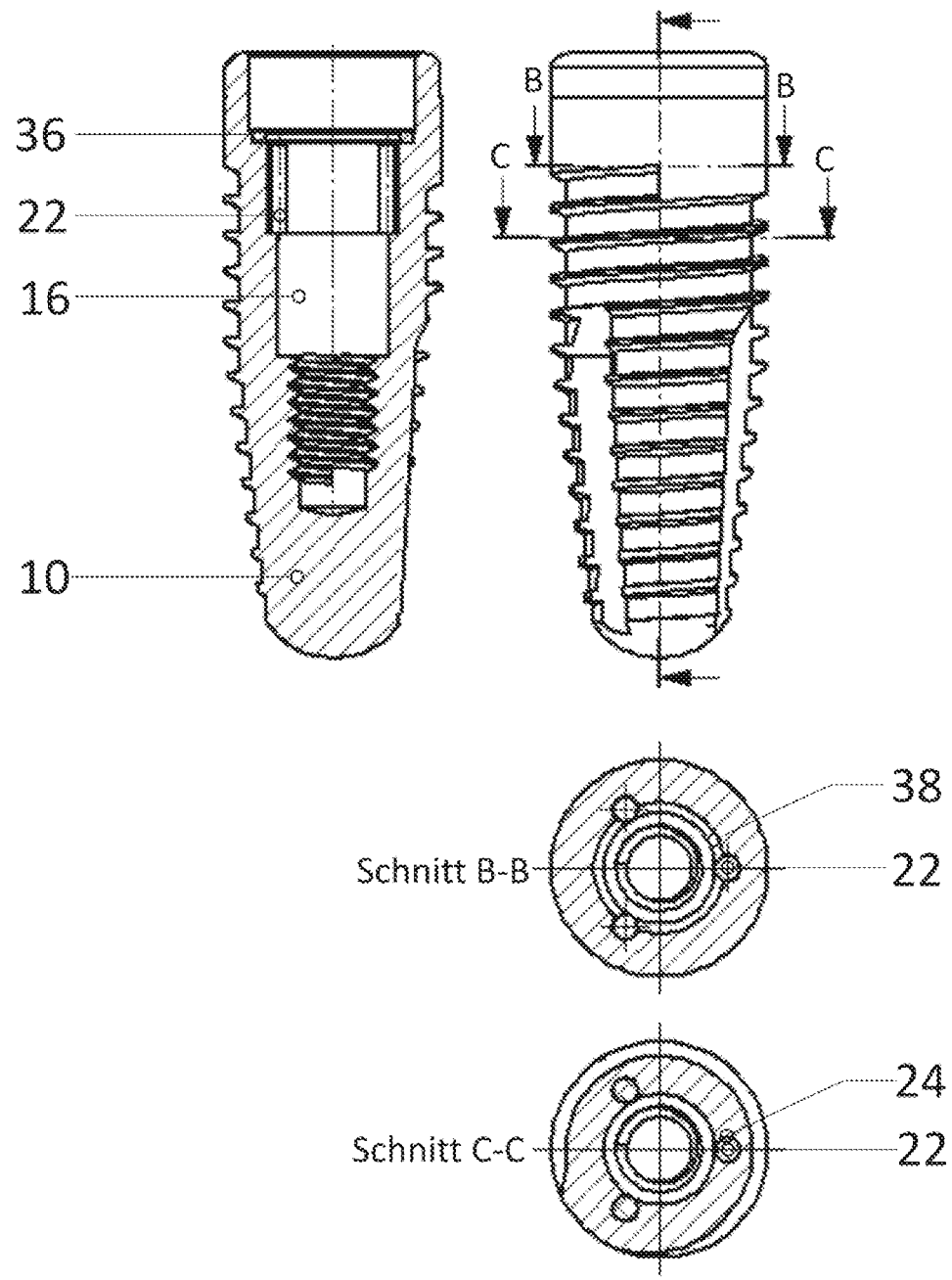
Figure 11:
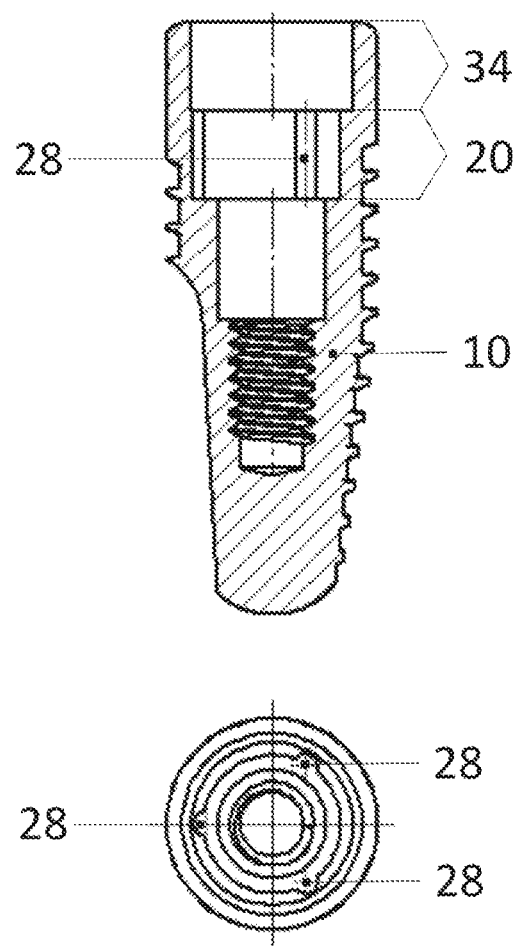
Figure 12:
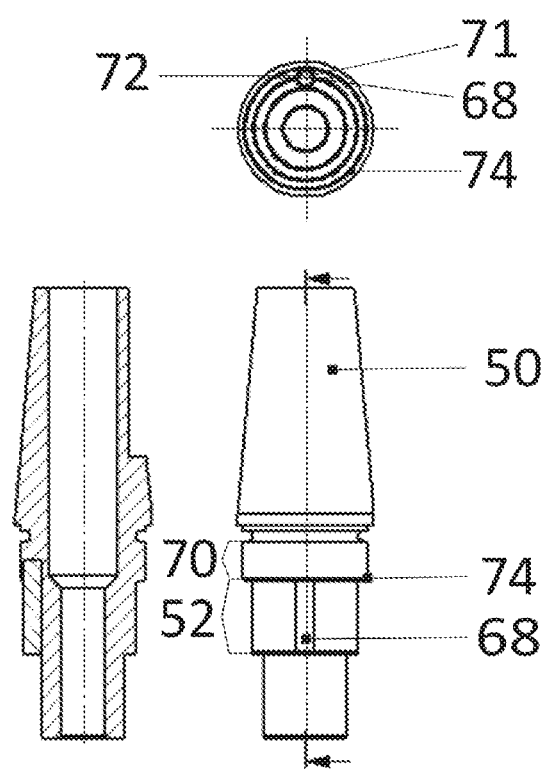
Figure 13:
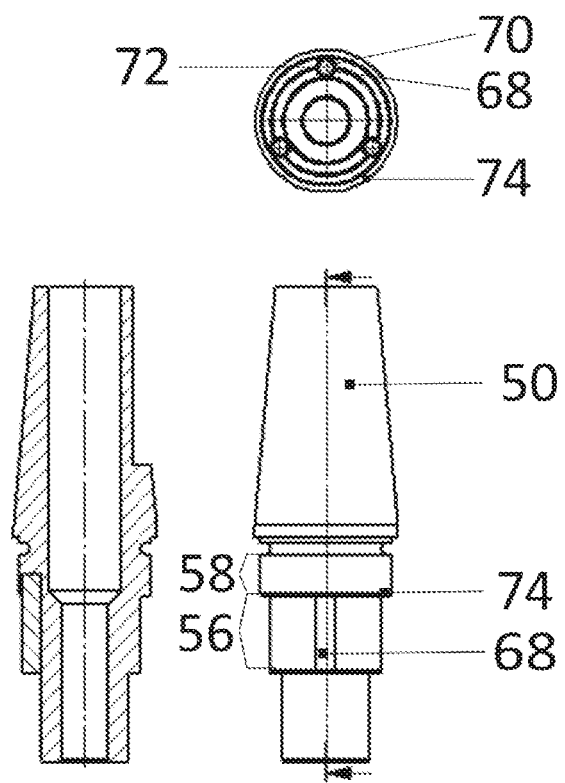

Embodiments by way of example of the single tooth implant according to the invention are described in detail hereinafter with reference to the diagrammatic drawings in which:

FIG. 1 shows in the upper part a plan view of an embodiment of the base body of the endosseous single tooth implant according to the invention in axial longitudinal section and in the lower part it shows a plan view of the base body from above, FIG. 2 shows a plan view of an embodiment of an abutment adapted to the base body of FIG. 1 of the single tooth implant in a view corresponding to FIG. 1, a longitudinal section in a plane perpendicular to the previous view and views on to the abutment coronally from above and apically from below, FIG. 3 shows in the upper part a plan view of a second embodiment of the base body of the endosseous single tooth implant according to the invention in axial longitudinal section and in the lower part it shows a plan view of the base body from above, FIG. 4 shows a plan view of an embodiment of an abutment adapted to the base body of FIG. 3 of the single tooth implant in a view corresponding to FIG. 3 with three tongues in axial longitudinal section, a longitudinal section in a plane perpendicular to the previous view and views of the abutment coronally from above and apically from below, FIG. 5 shows a plan view of a second embodiment of an abutment adapted to the base body of FIG. 3 of the single tooth implant in a view corresponding to FIG. 3 with a tongue in axial longitudinal section, a longitudinal section in a plane perpendicular to the previous view and views of the abutment coronally from above and apically from below, FIG. 6 shows in the upper part an embodiment of the base body of the endosseous single tooth implant according to the invention in axial longitudinal section and in the lower part a view of the base body from above, FIG. 7 shows an embodiment of an abutment adapted to the base body of FIG. 6 of the single tooth implant in a view corresponding to FIG. 6, a longitudinal section in a plane perpendicular to the previous view and views on to the abutment coronally from above (view below corresponding to DIN) and apically from below (view above), FIG. 8 shows in the left-hand part an embodiment of the base body of the endosseous single tooth implant of FIG. 6 according to the invention in axial longitudinal section along the plane identified by arrows in the right-hand part perpendicularly to the plane of the paper and in the right-hand part a view on to the base body and beneath same two sectional views radially to the longitudinal axis along planes B-B and C-C from above, FIGS. 9 and 10 show two partial views of the abutment of FIG. 7 of two embodiments, and FIGS. 11 to 13 show embodiments of the base body and the abutment of the tooth implant according to the invention with positively locking elements which are interchanged in respect of components in relation to the embodiments shown in FIGS. 6 to 11.

V. DETAILED DESCRIPTION OF THE DRAWINGS

As FIG. 1 shows the single tooth implant in the embodiment illustrated there has a base body 10.

The base body 10 which at its apical end shown below in FIG. 1 is of a closed configuration has a bore 12 which is open towards its coronal end which is upward in FIG. 1. Provided at the apical end of the bore 12 is a female thread 14 of small diameter, into which a holding screw (not shown in FIG. 1) can be screwed. Adjoining the female thread 14 of the base body 10 in the coronal direction is a frustoconical recess 16 of an inside diameter which increases in relation to the female thread 14.

In this arrangement the frustoconical recess 16 is in the form of a positively locking portion 20 which coronally adjoins the female thread 14 and which at the same time acts as a centering and guide portion which in the embodiment of FIG. 1 has three radially inwardly directed spring legs 26 and thus constitutes a positively locking portion. The spring legs 26 are of a configuration corresponding to the positively locking grooves 54 on the abutment 50 in the manner of a tongue-and-groove connection and can be of such a size that they extend over the entire axial length of the centering and guide portion 20. The spring legs 26 can be produced by machining from the base body. It is however advantageously also possible for the spring legs 26 to be formed by pins 22 being held in axial blind bores 24 in the portion 20, that are distributed uniformly around the periphery. In that case each of the pins 22 of a cross-section adapted to the blind bore 24, for example in the form of a cylindrical pin, can be so fitted into the bore 24 and embraced thereby in its end portion and held coaxially relative to the longitudinal axis of the base body 10, that a radially inwardly directed spring leg 26 corresponding to a positively locking groove 54 in the abutment 50 is formed. Preferably the blind bores 24 are arranged near the threaded portion and the thickness of a cylindrical pin held in the blind bore is so selected that the cylindrical pin 22 bears over its length against the portion 20 and is guided at least in a part of its longitudinal extent in a groove in the centering and guide portion/positively locking portion 20.

Adjoining the centering and guide portion/positively locking portion 20 in the coronal direction is an end portion having a coronal end ring 18. Preferably the end portion is only in the form of the coronal end ring 18 so that the positively locking portion 20 adjoins the coronal end ring 18. The end portion however can also be in the form of a cylindrical end portion.

The base body 10 can be easily manufactured by machining a blank. What is advantageous in that respect is in particular the fact that each tongue 26 is in the form of a respective pin 22 arranged in the blind bore 24 in the centering and guide portion/positively locking portion 20 of the base body 10. Thus, before the centering and guide portion 20 is formed, a respective bore can be bored coaxially with the blind bore 12 into the wall of the portion of the female thread, which remains when boring out the region 20 with a conical milling cutter in the form of a channel-shaped groove in the positively locking portion 20 and in the wall of the female thread, in the form of blind bores 24. A respective pin 22 which forms the tongue 26 can be axially fitted into that blind bore. It is however equally possible for the bores 24 to be produced by means of a milling tool in the hollow truncated cone. Although the use of cylindrical pins is advantageous in respect of manufacturing technology it is equally possible to use pins of a regular or irregular polygonal cross-section and a blind bore 24 correspondingly adapted in cross-section.

An abutment 50 shown in FIG. 2 serves as a fixing head for a fixed tooth replacement (not shown) and is provided with a fixing head 58 for the tooth replacement. Adjoining a shoulder 56 which can be fitted on to the base body 10 and which is in the form of a peripheral annular shoulder the abutment 50 has in the apical direction a centering and guide portion in the form a truncated cone 52 in which there is provided a number of axially extending positively locking grooves 54 which correspond in their shape and arrangement but not necessarily in their number to the tongues 26 of the base body 10.

When the abutment 50 provided with an axial longitudinal bore 60 whose inside diameter corresponds at least to the outside diameter of the holding screw (not shown) is inserted into the base body 10 the truncated cone 52 as the centering and guide portion of the abutment comes to bear against the hollow truncated cone 16 of the base body 10 and the abutment 50 is centred upon being further introduced. In that case the tongues 26 and grooves 54 are possibly brought into engagement with each other with rotation of the abutment 50 and the abutment 50 is thus secured to prevent it from rotating. It is advantageous if the tongues and the grooves have play relative to each other to such an extent that sealing portions preferably arranged in coronal relationship with the positively locking elements on the base body and the abutment can be brought into sealing interaction at the truncated cone 52 and the annular recess 16 in the form of the hollow truncated cone. In that case the sealing portion of the abutment 50, that adjoins the shoulder 56, preferably fits with a press fit in the end portion of the base body 10 near the end ring 18. As shown in FIG. 2, a groove 57 for receiving a seal like an O-ring can be provided in that sealing portion. The groove 54 can be formed by milling out using a conical milling cutter.

In that way the abutment 50 is connected to the base body 10 in non-rotationally fixed relationship. The abutment 50 can be connected fixedly and in non-rotationally fixed relationship to the base body 10 by means of the holding screw which passes through the abutment 50 and which can be screwed into the female thread 14 of the base body 10. To facilitate removal of the abutment 50 from the base body 10 a female thread (not shown in FIG. 2) can be provided in the bore passing through the abutment, wherein screwed into the female thread after removal of the holding screw is a forcing-off post (not shown) which is supported with its cervical end at the female thread 14 of the base body. When the holding post is screwed in the abutment 50 is then coronally lifted out of the base body 10 and can be removed.

Depending on the respective pitch or pitch ratio of the base body 10 and the abutment 50 respectively the abutment 50 can be inserted into the base body 10 in different rotational positions, for example in a degree graduation of 30°, 45°, 60°, 90°, 120° or 180°, whereby a number of different design configurations are available to the physician performing the treatment. In that respect the number of female part positively locking elements can be greater than the number of male part positively locking elements.

FIG. 3 shows a base body 10 of a structure which is modified in relation to the base body 10 in FIG. 1 insofar as the base body 10 in the positively locking portion 20 has three positively locking grooves 28 into which a respective corresponding tongue on the abutment can engage. In this configuration the base body 10 can also be easily manufactured by machining a blank. Thus, before the frustoconical-like region is formed for example three peripherally equally spaced bores can be bored coaxially at a predetermined spacing relative to the blind bore 12 in the positively locking portion 20 of the base body. When boring out the positively locking portion 20 with a conical milling cutter grooves are produced in the wall. If the diameter of the bore corresponds to the difference between the diameters of the circular surfaces delimiting the truncated cone (top surface and base surface) the grooves 28 are of a apically increasingly channel-shaped cross-section. Upon insertion into the base body 10 the abutment 50 can then be guided by way of tongues 53 corresponding to those grooves, on the abutment 50. The groove 28 can also be produced by milling out by means of a conical milling cutter.

An abutment adapted to the embodiment of the base body 10 shown in FIG. 3 and having the truncated cone 52 is diagrammatically shown in two partial views with three tongues 53 in FIG. 4 or with one tongue 53 in FIG. 5. As shown in the respective upper part of the above-mentioned Figures as a radial section, a respective pin is secured in the bore 55 to prevent it from axially falling out of same, for example by a press fit. Thus in this embodiment also the abutment according to the invention can be easily produced by machining a blank, in which case milling operations also have to be carried out for forming the positively locking elements.

As FIG. 6 shows the single tooth implant in the embodiment illustrated there has a base body 10 of the general kind as is described in a similar form for example in DE 195 34 979 C1.

The base body 10 which is of a closed configuration at its apical end shown downwardly in FIG. 6 has a blind bore 12 which is open towards its coronal end which upward in FIG.

6. Provided near the apical end of the blind bore 12 is a female thread 14 of small diameter, into which a holding screw (not shown in FIG. 6) can be screwed. Adjoining the female thread 14 of the base body in the coronal direction is a hollow-cylindrical annular recess 16 of an inside diameter which is enlarged in relation to the female thread 14. In the illustrated form the annular recess has three "stepped" regions (40; 20; 34) of different inside diameters.

In this arrangement the annular recess 16 has a centering portion 40 coronally adjoining the female thread 14. Adjoining the centering portion 40 of the annular recess 16 in the coronal direction is a positively locking portion 20 which is of an inside diameter that is increased in relation to the centering portion 40, and has a hollow-cylindrical inside wall with—in the embodiment as shown in FIG. 1—three radially inwardly directed tongues 26. The tongues 26 are designed to correspond to the positively locking grooves 66 on the abutment 50 in the manner of a tongue-and-groove connection and can be of such a dimension that they extend over the entire axial length of the positively locking portion 24. The tongues 26 can be produced from the base body by machining. It is however advantageously also possible for the tongues 26 to be formed by pins 22 being held in the positively locking portion 24 in axial holding grooves 25 distributed uniformly over the periphery. In that case each of the pins 22 of a cross-section adapted to the holding groove 25, for example in the form of a cylindrical pin, can be so fitted into the holding groove 25 and held partially embraced by the holding groove 25, that a radially inwardly directed tongue 26 corresponding to a positively locking groove 66 of the abutment 50 is afforded.

Adjoining the positively locking portion 20 in the coronal direction is an end portion 34 having a coronal end edge 38, wherein the end portion 34 is of an inside diameter that is increased in comparison with the positively locking portion 20. The end portion 34 has an inside wall which corresponds to the outside diameter of the sealing portion 70 of the abutment 50 and which can be cylindrical or conical. A securing ring 36 is fitted, for example with a press fit, in the end portion 34, at the region that is towards the positively locking portion 20. The inside diameter of the securing ring 36 corresponds at least approximately to the diameter of the positively locking portion 20, but however can also be somewhat larger. The securing ring 30 serves to prevent the pins 22 from dropping out of the groove 25 or bore 24. In a cylindrical configuration the end edge 38 serves as a height stop for the abutment while in a conical configuration the end portion 34, in the form of an internal cone, of the base body and the sealing portion 70 of the abutment, in the form of an external cone, serve as a height stop for the abutment.

The base body 10 can be easily produced by machining of a blank. It is advantageous in that respect in particular for the tongues to be in the form of respective cylindrical pins arranged in the blind bore 24 and associated groove 25 in the positively locking portion 20 of the base body 10. Thus before the positively locking portion is produced bores can be bored coaxially with the blind bore 12 into the wall 32 in the centering portion 40 of the base body, and remain when boring out the positively locking portion 20 as far as the shoulder ring 30 in the form of grooves 25 in the positively locking portion and also in the wall 32, in the form of blind bores 24.

Although the use of cylindrical pins is advantageous in terms of production engineering, it is equally possible to use pins of a regular or irregular polygonal cross-section and a groove 25 which is correspondingly adapted in cross-section, with blind bore 24 and matching positively locking groove 66.

An abutment 50 shown in FIG. 2 serves as a fixing head for a fixed tooth replacement (not shown) and is provided with a peripherally extending placement shoulder 61 for the tooth replacement. Adjoining a shoulder 59 which can be fitted on to the end edge 38 of the base body 10 and which is in the form of a peripherally extending annular shoulder the abutment 50 in the apical direction has a peripherally extending groove 63 for receiving a sealing means like an O-ring (not shown), a sealing portion 70, a positively locking portion 52 and a centering portion 62 with a centering shoulder portion 64. Provided in the positively locking portion 56 is a number of axially extending positively locking grooves 66 which correspond in their shape and arrangement but not necessarily in their number to the tongues 26 of the base body 10.

When the abutment 50 provided with an axial longitudinal bore whose inside diameter corresponds to the outside diameter of the holding screw (not shown) is inserted into the base body 10 the centering portion 62 engages with the centering shoulder portion 64 into the centering portion 40 of the annular recess 16, in which case the smooth cylindrical peripheral surface of the centering portion 62 comes to bear against the cylindrical peripheral surface of the centering portion 40 of the base body 10.

The sealing portion 70 of the abutment 50 preferably fits with a press fit in the end portion 34 of the base body 10. The tongues 26 engage into the positively locking grooves 66 while the shoulder 61 comes to bear against the end edge 38. In that way the abutment 50 is connected to the base body 10 in rotationally fixed relationship. The abutment 50 can be fixedly connected to the base body 10 by means of the holding screw which passes through the abutment 50 and which can be screwed into the female thread 14 of the base body 10. To facilitate removal of the abutment 50 from the base body 10 a female thread (not shown in FIG. 7) can be provided in the bore passing through the abutment, generally at the coronal end of the positively locking portion 52, into which there is screwed, after removal of the holding screw, a forcing-off post (not shown) with male thread, which is supported with its apical end at the female thread 14 of the base body. When the holding post is screwed in the abutment 50 is then coronally lifted out of the base body 10 and can be removed.

Depending on the respective pitch or pitch ratio of the base body 10 and the abutment 50 respectively the abutment 50 can be inserted into the base body 10 in different rotational positions, for example in a degree graduation of 30°, 45°, 60°, 90°, 120° or 180°, whereby a number of different design options is available to the physician performing the treatment. In that respect the number of abutment positively locking elements 66 is greater than that of the base body positively locking elements 28.

As shown in FIG. 8 illustrated in the sectional planes B-B and C-C are the pins 22 which are arranged in the blind bore 24 and which provide the tongues 26 projecting radially inwardly into the annular recess 16.

Two embodiments of the tongues can be seen by reference to two partial plan views of the abutment of FIG. 7 in FIGS. 9 and 10.

In FIG. 9 the tongue 26 is formed by the cylindrical pin 22 inserted into the blind bore 24 in the shoulder ring 30 and the groove 25. The corresponding positively locking groove 66 in the abutment 50 is of a cross-section like a segment of a circle in this embodiment.

As shown in FIG. 10 the tongue 26 can be afforded by the cylindrical pin 22 which is inserted into the groove 25 and can form a right-angle tongue 26. In this embodiment the corresponding positively locking groove 66 in the abutment 50 is also of a right-angled cross-section.

In the embodiments of FIGS. 9 and 10 the groove 25 embraces the pin 22 such that the pin on the one hand is held radially immovably in the groove 25 and on the other hand a radial portion of the pin projects out of the groove inwardly into the annular recess 16. To prevent axial movement of the pins 22 a securing ring (not shown in FIGS. 9 and 10) can be arranged in a press fit coronally on the pins 22.

FIG. 11 shows a base body 10 of a structure which is modified in comparison with the base body 10 in FIG. 6 in such a way that the base body 10 in the positively locking portion 20 has three grooves 28 into which a respective corresponding tongue on the abutment can engage. In this embodiment also the base body 10 can be easily produced by machining a blank. Thus, before the positively locking portion is formed, for example three peripherally equally spaced bores are bored coaxially at a predetermined spacing relative to the blind bore 12 in the positively locking portion 20 of the base body. When boring out the positively locking portion 20 as far as the shoulder ring 30 grooves 28 are produced in the wall 32 in the positively locking portion. If the diameter of bore corresponds to the difference between the inside diameter of the end portion 34 and the inside diameter of the positively locking portion 20 then the grooves 28 are of an approximately semi-circular cross-section, as shown in the lower part in FIG. 11. Upon being fitted into the base body 10 the abutment 50 can then be already guided in the cylindrical end portion 34 by way of tongues 68 on the abutment, corresponding to those grooves 28.

An abutment 50 adapted to the configuration of the base body 10 of FIG. 11, with a cylindrical end portion 70 and a positively locking portion 52, is diagrammatically shown in a number of partial views with one tongue 68 in FIG. 12 or with three tongues 68 in FIG. 13 respectively. As shown in the respective upper part of the above-mentioned Figures as a radial section, a pin 71 is secured in a bore (not shown) in a shoulder ring 74 to prevent it from falling out of the holding groove 72, for example as a press fit. Thus in this embodiment also the abutment according to the invention can be easily produced by machining a blank without complicated and expensive milling operations having to be carried out to produce the positively locking elements.

LIST OF REFERENCES 10 base body
12 bore
14 female thread
16 annular recess
18 end ring
20 positively locking portion
22 pin
24 blind bore
25 groove/bore
26 tongue
28 positively locking groove
30 shoulder ring
32 wall
34 end portion
36 securing ring
38 end edge
40 centering portion/guide portion
50 abutment
51 end ring
52 positively locking portion
53 tongue
54 positively locking groove
55 blind bore
56 shoulder
57 groove for receiving a seal
58 fixing head for tooth replacement
59 placement shoulder
60 bore for holding screw
61 placement shoulder
62 centering portion
63 peripheral groove
64 centering shoulder portion
66 positively locking groove
68 tongue
70 sealing portion
71 pin
72 holding groove
74 shoulder ring

The invention claimed is:

1. An endosseous single tooth implant for a fixed tooth replacement, comprising:
   a. a substantially cylindrical base body, which can be inserted into a bore made in a jaw bone, the cylindrical base body having an annular recess, a positively locking portion and a bore which is open towards a coronal end and which is arranged apically relative to the annular recess and which has a threaded portion which is arranged at the apical end in the base body for fixing a holding screw,
   b. an abutment which can be inserted into the recess of the cylindrical base body, said abutment having a positively locking portion, an axial longitudinal bore for receiving the holding screw and a fixing head for the tooth replacement, and
   c. a holding screw which can be inserted into the bore in the base body and which passes through the abutment,
   wherein the positively locking portion of the base body has at least one base body positively locking element operative in the peripheral direction and wherein the positively locking portion of the abutment has at least one abutment positively locking element complementary to the base body positively locking element,
   wherein the positively locking portion of the base body and the positively locking portion of the abutment are complementary to each other in such a shape that the abutment can be so inserted into the recess in the base body that the respective positively locking elements are brought into engagement with each other in the annular recess,
   wherein the mutually complementary positively locking elements are in the form of a radial male part—female part connection in the manner of a tongue—groove connection so that a tongue, which extends parallel to the longitudinal axis of the base body and which is provided on a component of the base body or the abutment, radially engages into a corresponding groove on the cylindrical base body or the abutment, thereby rotationally securing the cylindrical base body and the abutment, and,
   wherein the tongue comprises a pin held in an axial blind bore of the cylindrical base body or a pin held in an axial blind bore of the abutment.

2. A single tooth implant according to claim 1 in which the tongue comprises a pin held in an axial blind bore of the cylindrical base body.

3. An endosseous single tooth implant according to claim 2, comprising at least three tongues in the form of cylindrical pins held in respective axial blind bores distributed uniformly about a periphery of the positively locking portion of the cylindrical base body.

4. A single tooth implant according to claim 2, wherein the tongue is directed radially-inwardly to engage a locking groove in the abutment.

5. A single tooth implant according to claim 1, wherein the pin has a circular cross-section.

6. A single tooth implant according to claim 1 in which the respective male part is arranged on the base body and the corresponding female part is arranged on the abutment.

7. A single tooth implant according to claim 1 in which the respective male part is arranged on the abutment and the corresponding female part is arranged on the base body.

8. A single tooth implant according to claim 1, wherein the mutually complementary positively locking elements have with respect to the periphery of the base body and of the abutment a mutually matched 30, 60, 90 or 120 degrees graduation.

9. A single tooth implant according to claim 1, wherein the number of the female part positively locking elements is greater than that of the male part positively locking elements.

10. A single tooth implant according to claim 1, wherein the positively locking portion of the base body is in the form of a hollow truncated cone, wherein the longitudinal axis of the hollow truncated cone is coaxial with the longitudinal axis of the base body and the base surface of the hollow truncated cone faces towards the coronal end of the base body and wherein the abutment has a truncated cone corresponding to the hollow truncated cone.

11. An endosseous single tooth implant according to claim 10, wherein the hollow truncated cone of the base body has a cone angle of 6° to 18° relative to the longitudinal axis of the hollow truncated cone.

12. An endosseous single tooth implant according to claim 10, wherein the hollow truncated cone of the base body extends from the coronal end of the base body to the threaded portion for receiving the holding screw at the apical end of the base body.

13. An endosseous single tooth implant according to claim 10, wherein the hollow truncated cone of the base body has a cone angle of 10° to 16° relative to the longitudinal axis of the hollow truncated cone.

14. An endosseous single tooth implant according to claim 10, wherein the hollow truncated cone of the base body has a cone angle of 12° to 15° relative to the longitudinal axis of the hollow truncated cone.

15. An endosseous single tooth implant according to claim 10, wherein the hollow truncated cone of the base body has a cone angle of 14° relative to the longitudinal axis of the hollow truncated cone.

16. A single tooth implant according to claim 1, wherein the positively locking portion of the base body is in the form of a hollow cylinder, wherein the longitudinal axis of the hollow cylinder is coaxial with the longitudinal axis of the base body and wherein the abutment has a cylinder portion corresponding to the hollow cylinder.

17. A single tooth implant according to claim 16, wherein the positively locking portion of the base body is arranged cervically to the hollow-cylindrical end portion of the base body and is of an inside diameter which is reduced in relation to the end portion, and the abutment has a sealing portion corresponding to the end portion.

18. A single tooth implant according to claim 16, wherein adjoining the positively locking portion of the annular recess cervically is a centering portion of the annular recess of a diameter which is reduced in relation to the positively locking portion and the abutment has a centering shoulder portion corresponding to the centering portion.

19. A single tooth implant according to claim 17, wherein the sealing portion of the abutment and the end portion of the base body are in the form of mutually corresponding cones.

20. A single tooth implant according to claim 1, wherein the tongue comprises a pin held in an axial blind bore of the abutment.

21. A single tooth implant according to claim 20, wherein the tongue is directed radially-outwardly to engage a locking groove in the cylindrical base body.

22. A single tooth implant according to claim 1, wherein the tongue has a length that corresponds to a maximum axial length of the positively locking portion of the cylindrical base body or of the positively locking portion of the abutment.

23. A single tooth implant according to claim 1, wherein the groove on the cylindrical base body or the abutment extends along a longitudinal axis of the cylindrical base body or the abutment.

* * * * *